(12) United States Patent
Slotkin et al.

(10) Patent No.: US 12,702,728 B2
(45) **Date of Patent: *Aug. 11, 2026**

(54) PROACTIVE AIR/SURFACE DECONTAMINATION SYSTEM AND DEVICES

(71) Applicant: Radical Clean Solutions Ltd., Long Beach, NY (US)

(72) Inventors: Roger Slotkin, Long Beach, NY (US); Ralph T. Kubitzki, Plantation, FL (US)

(73) Assignee: Radical Clean Solutions Ltd., Long Beach, NY (US)

( * ) Notice: Subject to any disclaimer, the term of this patent is extended or adjusted under 35 U.S.C. 154(b) by 851 days.

This patent is subject to a terminal disclaimer.

(21) Appl. No.: 17/545,919

(22) Filed: Dec. 8, 2021

(65) Prior Publication Data

US 2023/0173127 A1 Jun. 8, 2023

(51) Int. Cl.
*A61L 9/20* (2006.01)
*A61L 2/10* (2006.01)

(52) U.S. Cl.
CPC . *A61L 9/20* (2013.01); *A61L 2/10* (2013.01); *A61L 2209/111* (2013.01);
(Continued)

(58) Field of Classification Search
CPC .................................... A61L 2/10; A61L 9/20
See application file for complete search history.

(56) References Cited

U.S. PATENT DOCUMENTS 2,945,554 A 7/1960 Berly
3,949,522 A 4/1976 Kehl et al.
(Continued)

FOREIGN PATENT DOCUMENTS

| | | | |
|---|---|---|---|
| JP | 2010080195 | A | 4/2010 |
| WO | WO2020176993 | A1 | 9/2020 |
| WO | PCT/US2022/051886 | A | 5/2023 |

OTHER PUBLICATIONS

LSE Lighting GPH450T5L/4P 4Pin Single Ended Ultraviolet UVC Preheated Lamp Bulb GPH450. Amazon.com. Accessed Jan. 16, 2025. On Sale since Mar. 21, 2014. (Year: 2014).*
(Continued)

*Primary Examiner* — Timothy C Cleveland
(74) *Attorney, Agent, or Firm* — Alfred M. Walker; Thomas A. O'Rourke; James Bongiorno

(57) ABSTRACT

A system for decontaminating/neutralizing breathable air and surfaces in an occupied enclosed space, i.e. building, aircraft, vehicle or greenhouse, includes mounting an atmospheric hydroxyl radical generator along an inside surface of the atmospheric hydroxyl radical generator having respective opposite air inlets and air outlets. The hydroxyl radical generator includes a polygonal housing supporting a plurality of spaced crystal-spliced UV optics, which are tubular, medical grade pure quartz optics to emit/irradiate ultraviolet in the nanometer wavelength/ultraviolet spectrum of between 100 and 400 nanometers for deactivating and neutralizing atmospheric chemicals and pathogens in breathable air and surfaces. The hydroxyl radicals contact the walls of the reaction chamber housing. The hydroxyl radicals become created and excited to react quickly with impurities including VOC, virus, bacteria and fungi, rendering them inactivated and neutral. The breathable air passes through the polygonal housing and is decontaminated and neutralized of impurities before entering the occupied enclosed space.

4 Claims, 8 Drawing Sheets

(52) U.S. Cl.
CPC ....... *A61L 2209/12* (2013.01); *A61L 2209/15* (2013.01); *A61L 2209/20* (2013.01)

(56) References Cited

U.S. PATENT DOCUMENTS

| | | | | |
|---|---|---|---|---|
| 6,497,840 | B1 | 12/2002 | Palestro et al. | |
| 6,613,277 | B1 | 9/2003 | Monagan | |
| 6,805,733 | B2 | 10/2004 | Engel et al. | |
| 7,416,588 | B2 * | 8/2008 | Burrows | A61L 9/20 422/24 |
| 7,837,933 | B2 | 11/2010 | Sevack et al. | |
| 7,976,195 | B2 | 7/2011 | Engel et al. | |
| 7,988,923 | B2 | 8/2011 | Fink et al. | |
| 8,226,899 | B2 * | 7/2012 | Woodbridge | A61L 9/20 422/186.04 |
| 8,252,099 | B2 | 8/2012 | Worrilow | |
| 8,252,100 | B2 | 8/2012 | Worrilow | |
| 8,545,753 | B2 | 10/2013 | Sevack et al. | |
| 8,747,753 | B2 | 6/2014 | Engel et al. | |
| 9,168,323 | B2 | 10/2015 | Morneault | |
| 9,522,210 | B2 * | 12/2016 | Worrilow | B01J 20/0222 |
| 9,675,725 | B2 | 6/2017 | Worrilow | |
| 9,884,135 | B2 | 2/2018 | Bystrzynski et al. | |
| 9,956,306 | B2 | 5/2018 | Brais et al. | |
| 9,980,748 | B2 | 5/2018 | Worrilow | |
| 10,857,249 | B2 | 12/2020 | Brais et al. | |
| 11,103,611 | B2 | 8/2021 | Elde et al. | |
| 2003/0099569 | A1 * | 5/2003 | Lentz | A61L 9/20 422/4 |
| 2008/0073565 | A1 | 3/2008 | Jeon | |
| 2015/0114822 | A1 | 4/2015 | Greco | |
| 2017/0225973 | A1 | 8/2017 | Henderson et al. | |
| 2020/0009286 | A1 * | 1/2020 | Zarcone | A61N 5/0618 |
| 2020/0084983 | A1 | 3/2020 | Liang et al. | |
| 2020/0129972 | A1 | 4/2020 | Ozaki et al. | |
| 2022/0176005 | A1 * | 6/2022 | Riesenberger | A61L 9/20 |

OTHER PUBLICATIONS

LSE (Light Spectrum Enterprises); "Shop UV Lighting-GPH457T5L/4P Ultraviolet UV Lamp Bulb 4-pin Base 18" GPH457T5; 1300 Industrial Blvd.-Ste B3, Southampton, PA 18966, 2021.

Hao Chen, et al.; "A Hydroxyl radical detection system using gas expansion and fast gating laser-induced fluorescence techniques"; The Research Center for Eco-Environmental Sciences, Chinese Academy of Sciences; Journal of Environmental Sciences 65 (2018) 190-200; published by Elsevier B.V.; http//dx.doi.org/10.1016/i.jes.2017.03.012.

GrowSaver™ by Sanuvox; "The Most Effective & Economical Way to Prevent Powdery Mildew"; download Jun. 24, 2022; https://growsaver.net/en/.

"Greenhouses/Heating, Cooling and Ventilation"; University of Georgia/Extension; Bulletin 792; reviewed Dec. 2014; extension.uga.edu.

Editor; "Canivate: Redefining the Standard for Cannabis Growth"; Canivate Growing Sytems Ltd.; last update Jul. 17, 2020; Business Television News; download Jun. 22, 2022.

* cited by examiner 40a
3
1
20
7
13
12
9
10

11
14
4
8
6
40a
3
13
12
15
1
20
9
10

4
14

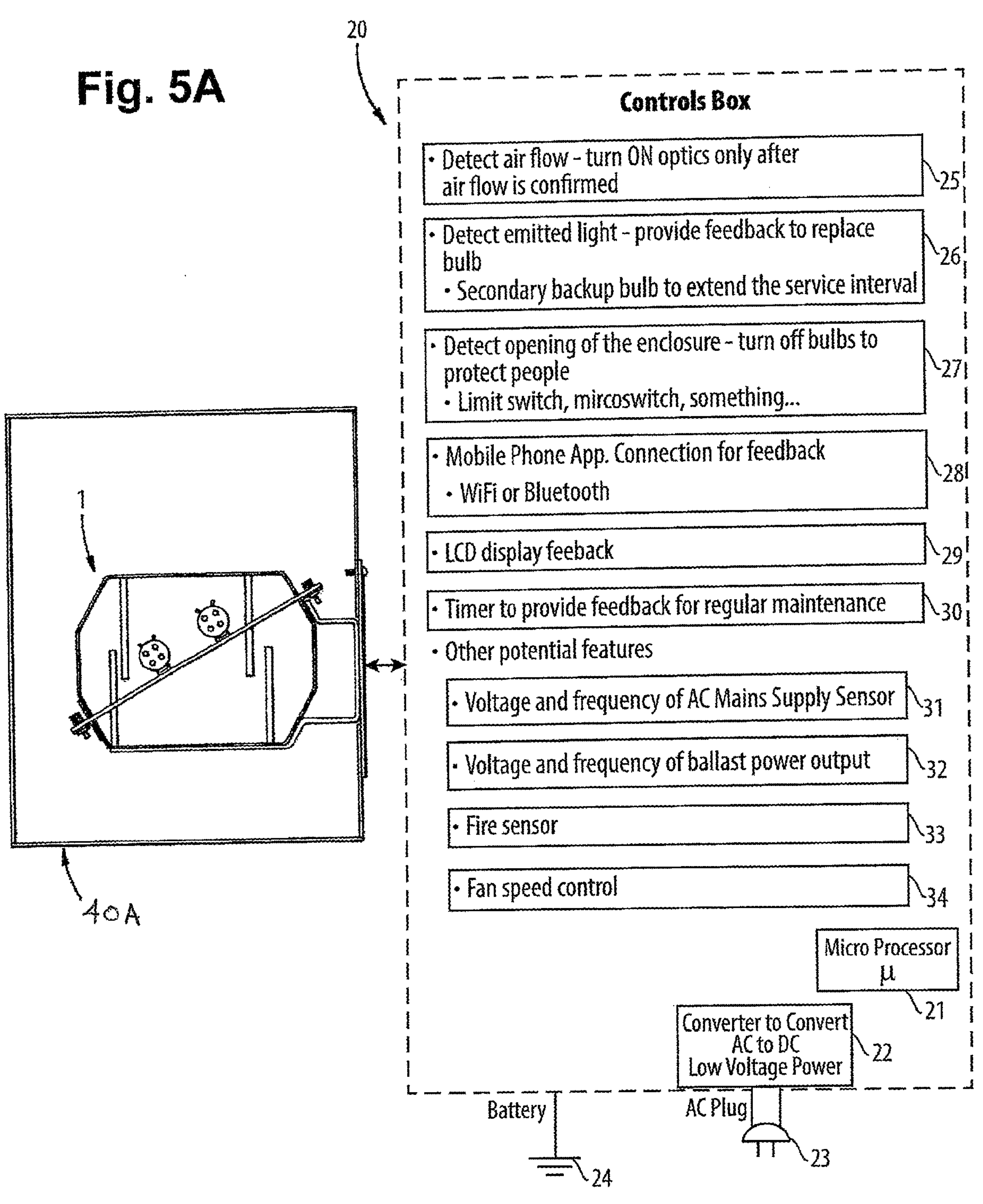
Fig. 5A
20
Controls Box
• Detect air flow - turn ON optics only after air flow is confirmed
25
• Detect emitted light - provide feedback to replace bulb
• Secondary backup bulb to extend the service interval
26
• Detect opening of the enclosure - turn off bulbs to protect people
• Limit switch, mircoswitch, something...
27
• Mobile Phone App. Connection for feedback
• WiFi or Bluetooth
28
• LCD display feeback
29
• Timer to provide feedback for regular maintenance
30
• Other potential features
• Voltage and frequency of AC Mains Supply Sensor
31
• Voltage and frequency of ballast power output
32
• Fire sensor
33
• Fan speed control
34
Micro Processor
μ
21
Converter to Convert AC to DC Low Voltage Power
22
Battery
24
AC Plug
23
1
40A 242
Air Path A
219b
219a
219
219c
201
212, 213
218
221
218a
218b
220
219e
218d
218c
Air In
218f
218e
218g
219d
240
245
240
219a
245a
245b
245c

241

330c
360
330
8A
8A
334
340
300
300a
370b
370a
341
370
330c
310
330d
300b
330b
330a
320
350
330
351

334
340
302
341
370b
360
370
370a
390
341
302

PROACTIVE AIR/SURFACE DECONTAMINATION SYSTEM AND DEVICES

FIELD OF THE INVENTION

The present invention relates use of a harmonic biomimicry nonchemical photonic process that results in the export of desired atmospheric hydroxyls at precisely the same rate as nature provides (2.6 million per cubic Centimeter—NASA), to neutralize toxic chemicals and pathogens in breathable air/surfaces in stationary or moving human occupied spaces.

BACKGROUND OF THE INVENTION

Ultraviolet light (UV) delivery in the form of directing ultraviolet light on unsanitary surfaces as germicides, bactericides and viricides are disadvantageous because, upon exposure to seating fabrics in aircraft and land vehicles, the ultraviolet light—compromises fabrics and doesn't penetrate into crevices between, or in, passenger seats. Delivery of ultraviolet light for sanitation is limited because the ultraviolet light is only as effective as the actual line of sight of the ultraviolet waves.

DESCRIPTION OF THE PRIOR ART

Methods of Producing Atmospheric Hydroxyls

In the field of physics there are, to date, only a few processes in a device that generates an atmospheric hydroxyl that purportedly are useful in removing contaminants from breathable air. In theory the NASA device produces the hydroxyl in a photo catalytic oxidation (PCO) process, by emitting an ultraviolet irradiation of 254 nanometers as it interfaces with titanium dioxide ($TiO_2$) plating. In theory, the hydroxyl is produced only at the interface site of contact at the surface of the $TiO_2$. The hydroxyl does not exit the airstream and does not have any downstream interaction. Minimal air flow must be maintained at approximately 120 cfm. Typical HVAC systems utilize faster air movement at approximately 2000 cfm and this would not allow for the theoretical hydroxyl to form.

OBJECTS AND SUMMARY OF THE INVENTION

In contrast, the present invention uses airborne hydroxyl radical molecules, which are of very small molar size and can occupy almost any given space. They can occupy dark crevices that ultraviolet line of sight cannot get access to. The present invention allows for a "Harmonic" of photonic UV frequencies to be applied within a hydroxyl producing reaction chamber. The feed stock is ambient water vapor in air which will have relative humidity, this humidity is the feed stock for the reaction chamber to produce the atmospheric hydroxyl.

This action is called "Bio-Mimicry". The present invention process is a totally green, nonchemical process that results in the export of the desired atmospheric hydroxyl at precisely the same rate as nature provides, namely, at 2.6 million per cubic centimeter. The atmospheric hydroxyl process begins by exposing ambient water vapor to special UV optics having hydroxyl activation portions made of medical grade pure quartz material. The optics are designed to emit/irradiate Ultraviolet irradiation in the nanometer wavelength/Ultraviolet spectrum of between 100 and 400 nanometers, thereby producing the hydroxyls at the aforementioned quantity of 2.6 million hydroxyls per cubic centimeter, as provided in nature. This is a novel improvement over prior art NASA PCO based technology.

Hydroxyl are groups having the radical "—OH" and are represented by the symbol —OH or HO—, which can have a negative charge or be neutral. The hydroxyl functional group includes one hydrogen atom which is covalently bonded to one oxygen atom. Hydroxyl radicals are very reactive, which react quickly to hydrocarbons, carbon monoxide molecules and other air impurities, such as volatile organic compounds, (VOC), virus, bacteria and fungi.

Many closed HVAC air systems can harbor microscopic bacteria, virus (i.e., Covid-19) and fungi.

For example, schools, nursing homes may have covid in the breathable air.

Also, aircraft and other transportation vehicles, such as railroad trains, can harbor bacteria and virus in the circulated cabin air systems.

Therefore, the present invention is a unique and novel application method of for the delivery of safe and natural hydroxyl radicals into breathable air volume containers such as airline or railroad cabins, and the contents therein. To be considered as well are upholstered chair seats, benches, contact surfaces such as grab bars, handles, etc.

In the present invention, the atmospheric hydroxyl radicals are generated in closed multi-sided housing, preferably polygonal, having therein two or more parallel UV optics which are multi segmented with crystal, so that when enabled, the hydroxyl radicals are generated. Hydroxyls are reactive and short lived, however the closed housing reaction chamber preferably has polygonal interior walls, so that the hydroxyl radicals will bounce against the walls so as to decontaminate within the reaction chamber as well as downstream in open air areas. Breathable air is then directed through the closed housing, so that the created and excited radicals will react quickly to air and surface impurities, such as pathogens and VOC's, rendering them neutral.

The UV optics are tubular, medical grade pure quartz. The optics are designed to emit/irradiate Ultraviolet irradiation in the nanometer wavelength/Ultraviolet spectrum of between 100 and 400 nanometers.

A multi wave 'Harmonic' is created via a multiwavelength nanometer configured optic irradiation. This configuration results in the creation of the desired atmospheric hydroxyl within the hydroxyl generator reaction chamber, which is a multi-sided reaction chamber, designed in such a way as to optimize atmospheric downstream hydroxyl production, such as for example in a polygonal-shaped housing. This multi-sided reaction chamber enables the desired atmospheric hydroxyl to be injected downstream to affect positive change. The positive change is the control/neutralization of pathogens and VOC's.

The —OH formed hydroxyl molecule is the capacitor that donates electrons to the targeted pathogen, whereupon the pathogen is therefore neutralized by the 'Electron Voltage (eV')' capacitance carried by the hydroxyl. The eV is donated at the point of contact with the pathogen.

VOC's are neutralized through the action of Bond Dissociation Energy (BDE). The capacitance of the charged hydroxyl is sufficient so as to take out of phase (decomposition) of any airborne molecular or compound structure. In Phase VOC chemistry can be harmful; therefore out-of-phase atomic airborne structures are now neutral and cannot recombine. The exception to this rule would be the recombination of water vapor, carbon dioxide and lastly oxygen (O2).

This reaction sequence is essential to all life, in that water vapor feeds all life, and carbon dioxide ($CO_2$) is necessary/essential for plant life and oxygen ($O_2$) is essential for air breathers such as human, other animals and forms of living organisms.

EXAMPLES

Aircraft:

Atmospheric Hydroxyl radical generators can be externally fastened to and otherwise added into aircraft air conduits, which, for safety reasons, provide breathable cabin air through a flexible (typically yellow) conduit from a source external to the aircraft, to avoid engaging the generator at the site of the aircraft tarmac. Hydroxyl radicals (added to the breathable cabin air) are provided from a retrofit device and vectored into the cabin of the aircraft. This is an improvement over the cleanup of aircraft cabin air and cabin surfaces, which is usually done with inadequate delivery of UV light from a portable cart, which can only disinfect exposed surfaces, not the general volume of breathable air and the crevices between seats and other surfaces, as well as behind grab bars and other semi-hidden surfaces. However, in the present invention hydroxyl radicals are directed into the aircraft air supply conduit and then into the zones of air within the aircraft where for safety reasons, which include biological and chemical intrusion, the air in the flight deck is completely separate from the passenger cabin air. This may also include the installation of generators of hydroxyls in cabin air circulation systems in the aircraft itself.

Buildings:

Hydroxyl radical generators can be installed within HVAC ducts in a building, where an access port is created within the air duct, and the hydroxyl generator or generators are secured in place within the building HVAC system.

Portable Units:

Smaller portable units that roll in place in small rooms on casters, with a hydroxyl-generator therein, can have blowers to direct atmospheric hydroxyl treated air into residential, school or nursing home rooms. These consumer units include a multi-sided Reaction Chamber, preferably polygonal (hexagonal or octagonal shape) to maximize ultraviolet refraction while interacting with the incoming breathable air. Blowers, such as Squirrel cage air system with a spinning, drum direct the air through the portable unit and thence into the reaction chamber. The portable consumer unit also has a Filter swap out system, with an easy 'Swap Out' of a High Efficiency Filtration System. The housing is an integrated chassis, with an air pathway input/output hookup. The housing also has a removable disengage chamber with a release mechanism, to take out the reaction chamber for maintenance. The reaction chamber cannot be maintained in situ within the housing of the portable unit.

Because exposure of the UV light is problematic for human eyes, the interior of the reaction chamber is custom designed to arrest UV light escaping and to maximize atmospheric hydroxyl discharge. Refraction color can come out of the unit with the generated, activated hydroxyls, but never direct UV light.

The portable unit also has a unique Internal Air Baffling System, to promote the zig zag of air movement therein, to control light and prevent unwanted UV light from escaping so that the breathable air passes through the portable unit. The unique device design does not allow for any UV light to exit the unit.

Available hydrogen is low in our natural environment, so one must add electron rings to obtain optimal amplitude as opposed to adding hydrogen for increased hydroxyl production.

The portable units were targeted to emulate certain characteristics required within the hospital framework. Pathogen and VOC control is of paramount concern and is inherent within the design parameters of the hydroxyl generating device.

Consideration was also made with regard to sound control, wherein low air flow volume of 110 cubic feet (cf) must be quieter than 30 decibels or below (Hospital Quiet).

The portable units also contain an optimal-UV light refraction tubular fan assembly, which draws in the incoming air into the hydroxyl generator chamber housing. Baffles located in the portable and duct installed hydroxyl generators allow air through the hydroxyl generator but prevent exposed UV light from escaping. The sole purpose of the baffles is to arrest any UV rays from escaping the device. Any direct line of sight to the UV source would cause a "Welders Flash" incident and may temporarily harm the eyes of the observer. This type of incident is simply not allowed and is part of the safety investigation of the validation bodies UL/CSA.

The polygonal shape of the reaction chamber enhances the total ability of the chamber to produce the desired atmospheric hydroxyl.

It is essential that the atmospheric hydroxyls be produced by the exposure of ambient water vapor within a confined refractive generator chamber housing to prevent diminution of the atmospheric hydroxyls. In contrast, SanUVox, by using outward facing reflectors but no confined generator chamber housing, causes a drastic diminution of the desired hydroxyl production.

In contrast the present invention, by using the polygon shaped reaction chamber, has categorically enhanced atmospheric hydroxyl production.

The portable units also have communications capabilities, so that the Hydroxyl Generating Device can interface with a remote-control pad or mobile phone.

Safety features include a microswitch which will shut off from inadvertent opening if the reaction chamber device is "on" when it should be "off". The micro switch shuts down all systems should the device be opened when the generating unit is in operational status.

Anti-Vibration G-Force Mitigation Clips are installed, such as spring clips which operate in only one directional installation.

Reactor Rod Safety is paramount, for prevention of Reactor Rod displacement and breakage.

The portable unit also includes custom designed noise reduction adhesive pads, and strategically placed self-adhesive sound/vibration reduction material wall insulation to mitigate sound and vibration.

Large Building Installations:

Large Building HVAC units have the above features, but where the optics are provided in a two optic array of a-b options, where "A" is on, but "B" is on if A fails.

No fan assembly, as is the case with the portable unit, is needed because the HVAC system has its own air movement capability. In a double optic option one optic may be on to create the hydroxyl radical and the existing HVAC fan directs the hydroxyls with the dual optic availability, should there be an abnormal intrusion of VOCs' or pathogens into the HVAC system, then the sensor would alert the hydroxyl device and the second optic would then come online in order to neutralize the threat load.

For safety, an air pressure safety switch is provided, so that when air flow is not detected, this unit will be dormant. A Micro Switch shuts down all systems should the device be opened when unit is in the ON/RUN position.

Greenhouse Hydroponic Installation

In hydroponic or other greenhouses, as in Nature, the atmospheric hydroxyls are lighter than air, so they are provided below plant growing media, such as of coconut fiber, vermiculite, etc., wherein the hydroxyls located from below flow up around the roots and growing media; being lighter than O2, the hydroxyls "drift upward". They will not penetrate fluid or solids, so parts of the roots and media must be exposed to hydroxylated air, as opposed to being in fluid or soil. This greenhouse installation also uses a 2×2 lamp array and has the same options as in the large building HVAC duct installation.

BRIEF DESCRIPTION OF THE DRAWINGS

The present invention can best be understood in connection with the following drawings, which are not deemed to be limiting in scope.

FIG. 5A is a flow chart showing the electronic controls with respect to their position adjacent to the hydroxyl generator.

DETAILED DESCRIPTION OF THE DRAWINGS

Figures 1, 2:
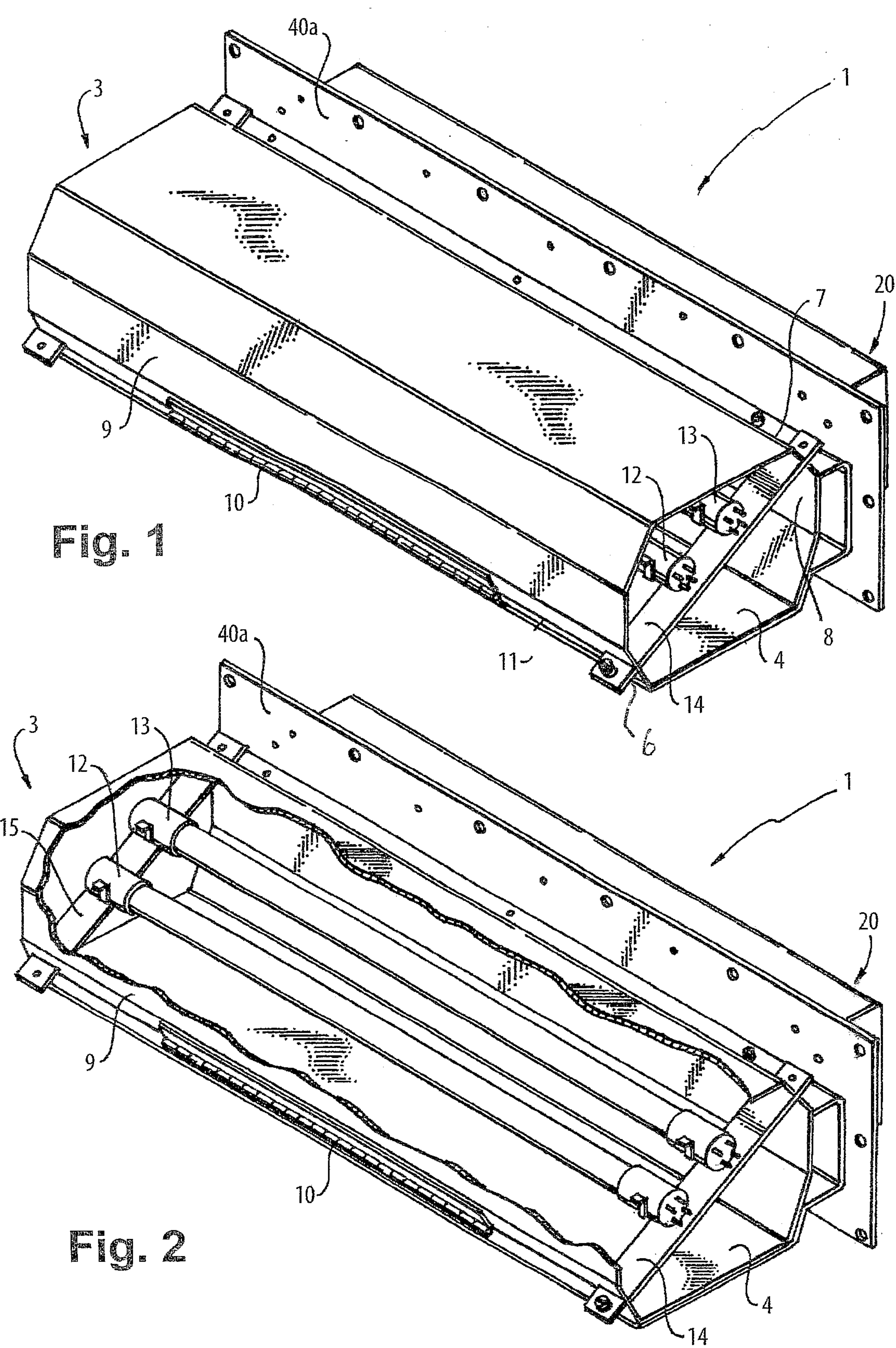
FIG. 1 is a perspective view of a polygonal hydroxyl generator shown in a closed position.
FIG. 2 is a perspective view of the hydroxyl generator of FIG. 1 shown in partial crossection with an open view of the interior of the hydroxyl generator.
Figure 4:
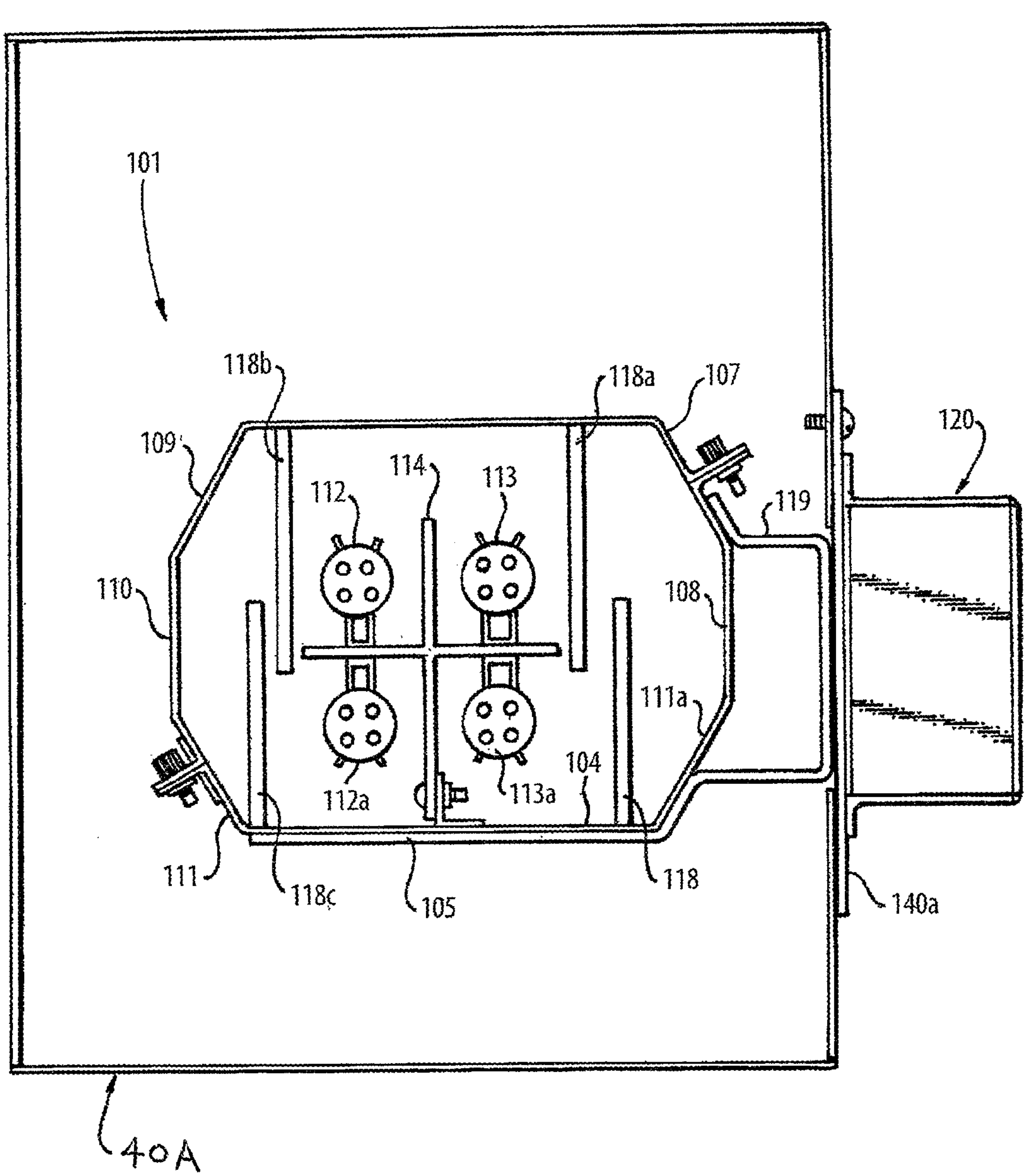
FIG. 4 is a crossectional end view of an alternate embodiment for a hydroxyl generator, showing four UV hydroxyl generator optics within the polygonal hydroxyl generator.

FIG. 1 shows a hydroxyl generator 1, including a polygonal-shaped housing, including a bracket brace 14 for crystal-spliced UV optics 12 and 13 (and a bracket 114 for UV optics 112, 112*a*, 113, and 113*a* shown in FIG. 4), which crystal-splices UC optics are mounted parallel to each other inside the clamshell hexagon housing, wherein the crystal spliced UV optics 12 and 13 each have a length that runs substantially the entire length of the housing of the hydroxyl generator 1. As shown in FIG. 4, the mounting bracket 114 may have a first flange and a second flange, with the first flange secured to a side of the clamshell housing in proximity to a first end of the housing, and with the first flange extending perpendicular to that side of the housing; a first flange of a second mounting bracket may be secured to that side of the housing in proximity to a second end of the housing. As seen in FIG. 4, the first end of the four UV lamps may each be secured to the top and bottom surfaces of the second flange of the first mounting bracket 114 at the first end of the housing using a respective UV lamp fastener, i.e., using first, second, third, and fourth UV lamp fasteners; and the second end of the four UV lamps may also be secured to the top and bottom surfaces of the second flange of the second mounting bracket at the second end of the housing using a respective UV lamp fastener, i.e., fifth, sixth, seventh, and eighth U.V. lamp fasteners. As shown in FIG. 4, the generator mounting bracket 119 may be formed with a first flange, and a second flange and a third flange each extending perpendicularly away from respective distal ends of the first flange for thereby forming a channel-shaped cross-section, and with a fourth flange extending away from a distal end of the second flange, a fifth flange extending away from a distal end of the third flange, and a sixth flange extending away from the end of the fifth flange, where the third flange and the fourth flange may be at angles matching first and second sides of the octagonal-shaped housing, and the sixth flange may be at an angle matching and supporting a bottom of the housing. A preferred example for the crystal-spliced UV optics 12 and 13 is the GPH457T5L/4P UV Optic 4-pin Base 18" GPH457T5 of Light Spectrum Enterprises of Southampton these optics 12 and 13 are typically 18 inches long and are made of quartz. The tubular optics 12 and 13 are composed of pure Medical Grade quartz crystal in the portion of the optics which creates the hydroxyls. The present invention adds additional frequencies to the pure crystal optics. This tubular lamp optics 12 and 13 generate 'Harmonic' bio-mimicry nonchemical process of the present invention enables the production of desired atmospheric hydroxyls at a rate commensurate with the VOC/Bio loading in that particular space to be treated with the hydroxyls.

In contrast to the medical grade quartz tubular optics, it is noted that total glass tubes cannot be used when generating UV. The glass would simply be vaporized. Some companies use a fusion of glass and quartz crystal, which is not optimal as the glass portion creates a frequency that actually attracts contaminants. This problematic action neutralizes the desired UV action. Such a fusion lamp of glass and quartz crystal is cheaper to produce, however the poor performance of the lamp would be the end result.

Figure 3:
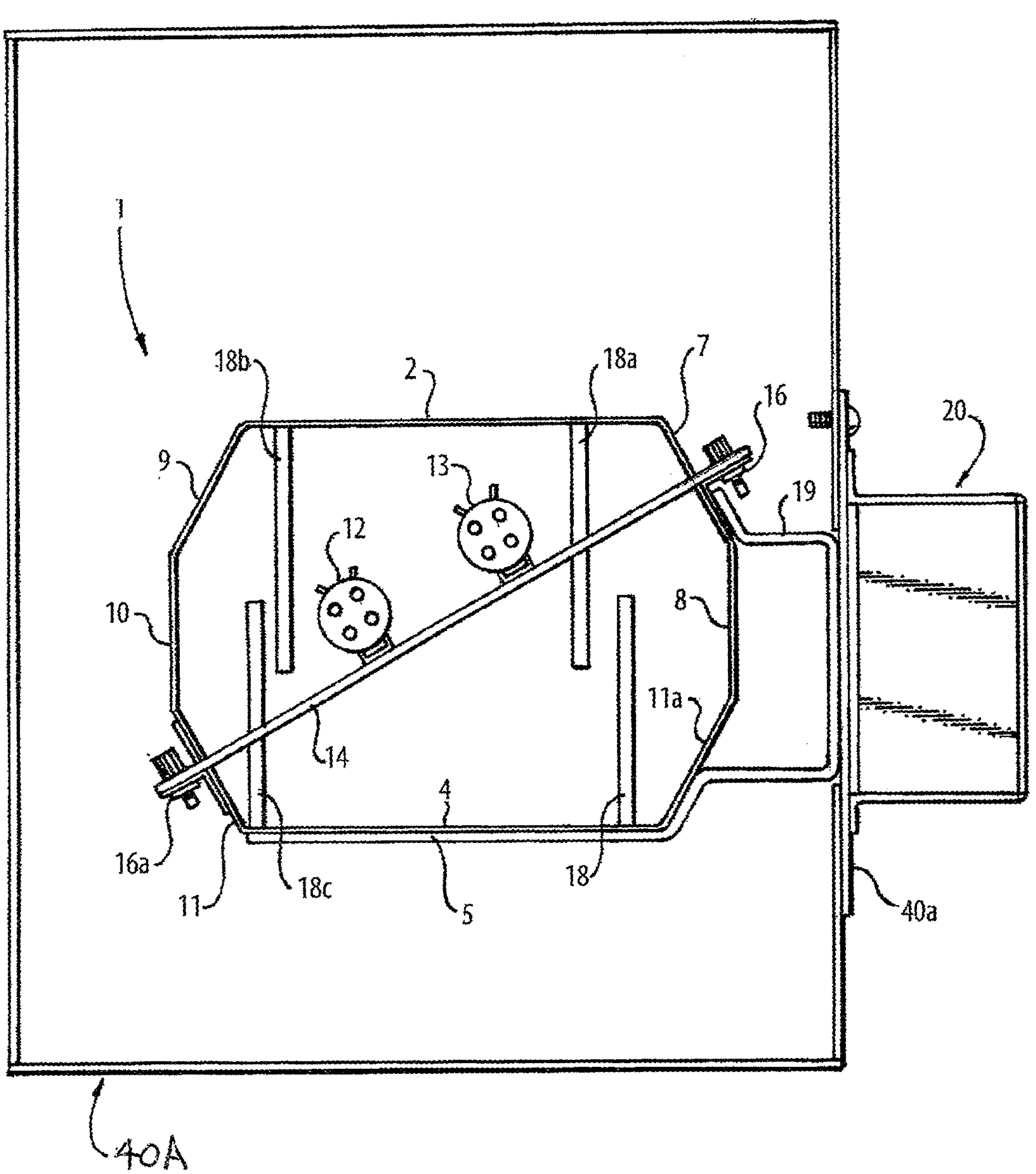
FIG. 3 is an end view in crossection of the hydroxyl generator of FIG. 1, with two UV optics for generating hydroxyl radicals.

Other similar Medical Grade quartz tubed UV optics can be used. The optic 12 and 13 are preferably symmetrically positioned in the housing of the hydroxyl generator 1, as shown in FIGS. 3 and 4 to operate most efficiently, which housing may include overlapping internal baffles 18, 18*a*, 18*b*, and 18*c*, to limit any leaking of UV light from the crystal-spliced tubular optics. The clamshell hexagon housing hydroxyl generator 1 has a clamshell configuration, including a clamshell top wall 2, upper side walls 7, 8, 9 and 10, a hinge 6 for opening the polygonal clamshell housing land a bottom clamshell portion, including a bottom wall 4 and angle-oriented walls 11 and 11*a*, whereby the polygon housing opens hinge 6 to expose the inside of the hydroxyl generator 1 for maintenance and/or repair. In addition, the polygon hydroxyl generator enclosure can be removed from the air duct wall 40A for such maintenance and repair. The hydroxyl generator also includes an adjacent electronic control box 20, which is attachable to the clamshell housing of the hydroxyl generator 1. Alternatively, as shown in FIGS. 3 and 4, the electronic control box 20 is preferably located outside of the air path, which may be a duct or other conduit. It can alternatively be attached outside of the duct. It communicates with the UV optics wirelessly. The reason for the polygon shape is that the hydroxyl generators generated by the crystal-spliced UV optics 12 and 13 are scattered upon being generated by the optics 12 and 13, but they dissipate quickly if not activated by contact with reflective non-absorbent surfaces inside the respective walls of the polygon. The purpose of the polygon shape is that when the hydroxyl radicals are generated, they are emitted radially in all directions from the UV crystal-spliced optics 12 and 13 and normally would dissipate when scattered radially from the optics. In order to permit the hydroxyl radicals to maintain their desired electron charge and ability to contact and inactivate mold, volatile organic compounds, pathogens, bacteria, virus, etc., they need to reflect and refract off of the reflective non-absorbent walls continuously, within reaction chamber confined space. As atmospheric hydroxyls are being activated by being created and excited in back-and-forth activity, the air inside the air duct/plenum 40*a* will contact the activated hydroxyl radicals with the end result of the neutralization of any impurities, such as VOCs, virus, bacteria, fungi, etc., in the air and surfaces.

Furthermore, once these radicals are emitted, they can penetrate any crevices in any area, such as between seats of mass transit vehicles, between the surfaces of desks; anywhere where ultraviolet light by itself would not be capable of eradicating the undesirable VOCs, fungi, virus, bacteria, etc. The polygon-shaped housing is strategically located within an air duct wall, which can be in a building which has sub walls extending to various rooms in the building, or it can be into the central area of a mass transit railroad or other mass transit vehicles, or it may be provided in the three air systems of an aircraft cabin, including the flight deck and the areas of the main cabin where passengers are seated.

As shown in the end view of FIG. 3, the inside of the polygon housing 1 is located below the field of vision within the sealed off plenum so that the ultraviolet (UV) crystal-spliced tubular optics 12 and 13 will not be exposed to the eyes of any observers. Therefore, while the hydroxyl radicals are being generated, the UV energy which create hydroxyl generation from optics 12 and 13 are completely sealed off so that when the optics 12 and 13 are operational, the UV light emanating therefrom will not penetrate outside of the polygonal housing. There is no restriction regarding the active flow of the hydroxyls inside the hydroxyl generator 1 and no interference with the excitement of the hydroxyls produced by the exposure of ambient water vapor within the polygon shaped housing with the UV optics 12 and 13 irradiating light that causes the —OH radicals to form.

FIG. 4 shows an alternate embodiment for a four optic version, where polygon hydroxyl generator enclosure 101, having top wall 102, side walls 107, 108, 109, 110 of an upper shell, as well as lower walls 105, 111*a*, 111*b* of the clamshell housing. FIG. 4 also shows the electronics control box 120.

Figure 5:
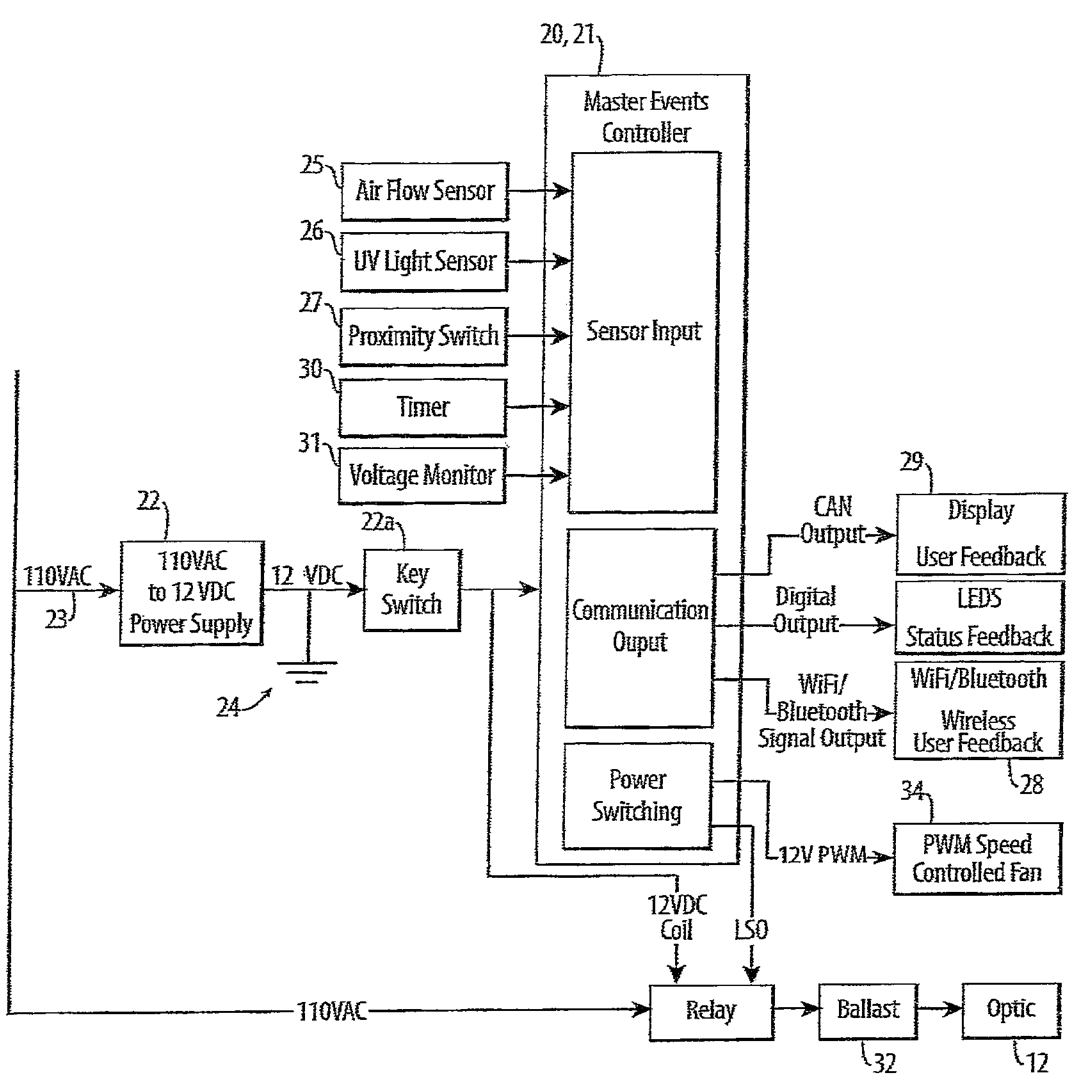
FIG. 5 is a block diagram of the electronic controls of the hydroxyl generator of FIGS. 1-3 and 4.

FIG. 5 is a block diagram showing the network and electronics of the control box 20. Initially AC power 23 of 110 VAC is converted by converter 22 to low voltage 12 VDC, or else a low voltage battery alternatively delivers 12 VDC to a secure Key Switch 22*a*, to provide power to the Master Events Controller 20, which may have a microprocessor 21. The Master Events Controller 20 also receives input from sensors, such as Air Flow Sensor 25, UV Light Sensor 26, Proximity Switch 27 (detecting opening of the enclosure), Timer 30 and Voltage Monitor Sensor 31. These sensors provide Sensor Input to the Master Events Controller 20. Power Switching in the Master Events Controller 20 sends 12V Pulse Width Modulation data to a PWM Speed Controlled Fan 34, to send air through the hydroxyl generator unit 1 or 101, or to stop the flow of air when needed for safety and maintenance situations. The Power Switching also sends data via a Large Serve Outlet (LSO) to a Relay, which controls the Ballast 32, providing power to the Crystal UV Optics 12, which creates the needed hydroxyls within the hydroxyl generators 1 or 101. The Master Events Controller 20 also has a Communications Output, which can send data via a Controller Area Network (CAN) to a Visual Display 29 for user feedback. The Communications Output of the Master Events Controller 20 also sends digital data wirelessly as output to Status Feedback Units. The Communications Output of the Master Events Controller 20 also sends Wi-Fi/Bluetooth Signal output to Wireless input devices 28 for Wireless user feedback during use.

FIG. 5A is a diagrammatic flow chart, showing the electronic control box 20 of FIGS. 1, 2 and 3, which is also equivalent to the electronic control box 120 of FIG. 4. Adjacent to the hydroxyl generator 1 or 101, which in FIGS. 1-3, the hydroxyl generators are attached by brackets 19 to the electronic control box 20. Similarly, the electronic control box 120 is attached by brackets 119 of FIG. 4.

In the diagrammatic flow chart of FIG. 5A, related to the electrical block diagram of FIG. 5, the control box 20 includes a microprocessor 21 for controlling the sensors and switches, which control the operation of the optics 12 and 13, or 112 and 113, of FIGS. 1-3 and 4. There is also a power source being either a DC low-voltage battery 24, or an AC plug 23, to provide higher-voltage AC power. When the AC is used, a converter 22 can be provided to convert high-voltage AC to low-voltage DC power for operating any of the sensors and control elements within box 20. The controls include a detector 25 to detect whether airflow is on, so that the optics 12 and 13 will only be on after airflow is confirmed, so that they are not on when there is no airflow. In the sensor for detecting emitted light, and providing feedback to replace optics, including a secondary backup optic, is provided at box 26 of the flowchart. Box 27 is a detector for opening of the enclosure, to turn off the optics to protect people from being exposed to the possible harmful UV light emitted from the optics 12 and 13. This detection also includes a limit switch, a micro switch and sensors. Box 28 is a mobile phone application for connection for feedback by wireless communication, such as Wi-Fi or Bluetooth® communications between the operator and the control box and hydroxyl generator itself. The control box also includes an LCD display feedback system 29, as well as a timer 30 to provide feedback for regular maintenance. Voltage and frequency of AC main supply sensor 31 is provided and voltage and frequency of the monitor of the ballast and power outfit 32 is also provided. A fire sensor 33 detects excess heat in the system and a fan speed control 34 controls any fans for providing and activating the airflow through the polygon hydroxyl generators.

Figures 6, 7:
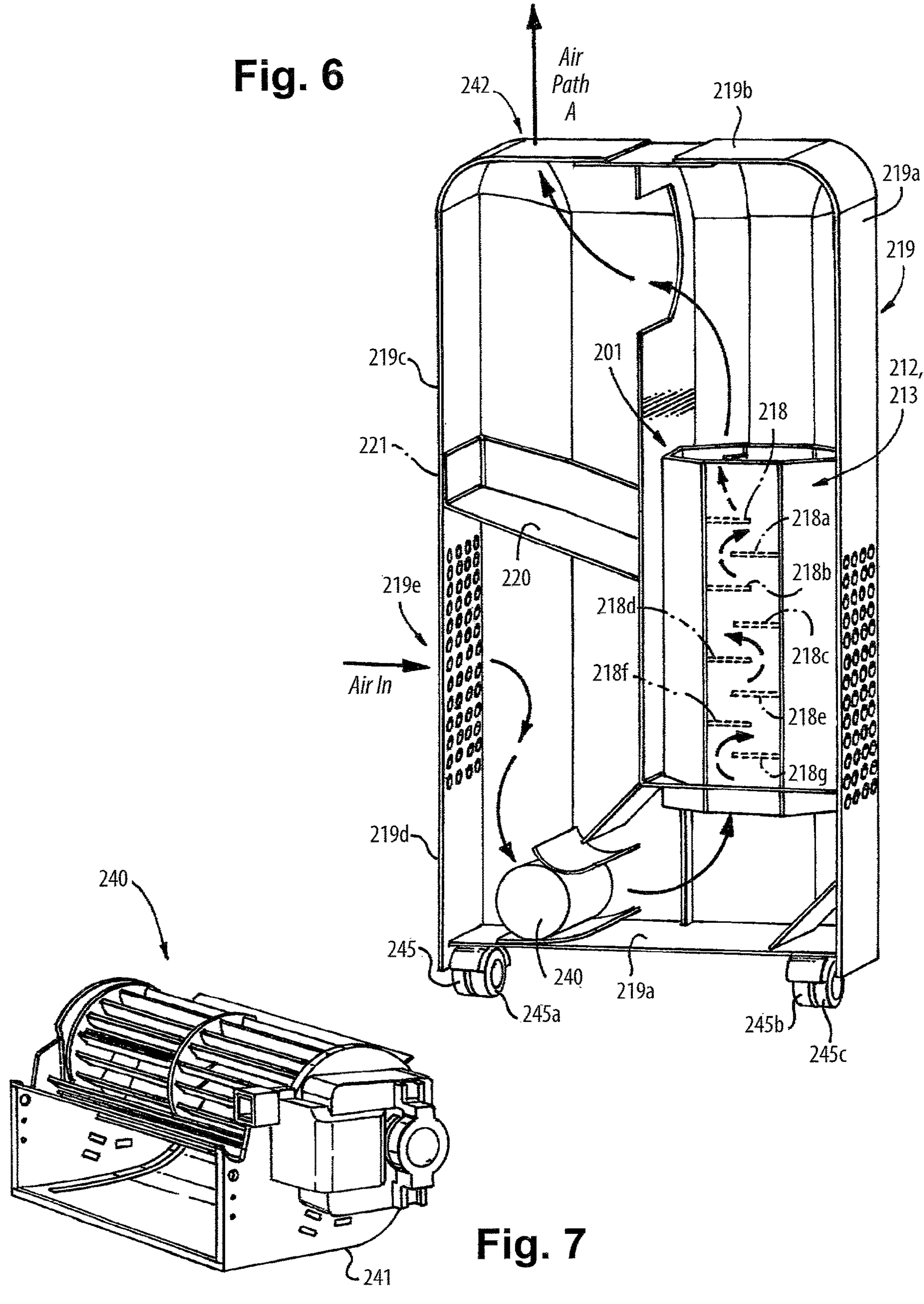
FIG. 6 is a perspective view in partial crossection of a standalone hydroxyl generator chamber housing mounted on movable member, such as wheels or casters.
FIG. 7 is a closeup perspective view of the airflow blower of the portable unit of FIG. 6.

While FIGS. 1-4 show polygon hydroxyl generators 1 or 101, which are removably positioned within air ducts of a building, or other enclosure, for lower power needs in smaller confined areas, such as individual rooms in a building or schoolhouse or nursing home, FIG. 6 shows a portable unit which can be provided, which will have a smaller interior volume for producing the optimal number of hydroxyls generated to purify the air/surfaces and crevices/creases within the aforesaid areas. Such a portable hydroxyl generator includes a generator chamber housing 201, which is mounted on a bottom wall, including casters or wheels 245, 245*a*, 245*b* and 245*c* on the bottom for moving the hydroxyl generator 201 around in a confined space area, such as an individual room. The movable generator 201 also includes the polygon generator chamber housing 201, which has inside the optics 212, 213, and overlapping internal baffles 218, 218*a*, 218*b*, 218*c*, 218*d*, 218*e*, 218*f*, and 219*g*, again, to limit any leaking of UV light from the crystal-spliced tubular optics (and baffles 18, 18*a*, 18*b*, and 18*c* in FIG. 3, and baffles 118, 118*a*, 118*b*, 118*c*, and 118*d* in FIG. 4), which upon being engaged will generate the hydroxyl radicals flowing nearby. The unit 200 also includes an air intake 219*e*, as well as a partition and space for the electronics 220, an air blower 240 which blows and pressurizes air to the chamber of the hydroxyl generator 201. Front bezel 221 is provided for controls and the air intake 219*a* is provided on one of the walls 219*c* of the aluminum unit 219, enclosing the housing generator 201. The aluminum cover, or other suitable material, has side walls 219*a*, 219*c*, top wall 219*b* and bottom wall 219*d*, as well as rear wall 219E and front cover (not shown). When the aluminum cover is removed, it provides easy access for optic cleaning and/or replacement of the hydroxyl generator 201, which can be taken out and opened along its clamshell hinge 6 or 206. The air is passed through the intake, blown by the blower 240, then through the polygonal generator chamber housing 201 and out through an air outlet 242. The blower 240 is mounted by a mount 241.

Figures 8, 8A:
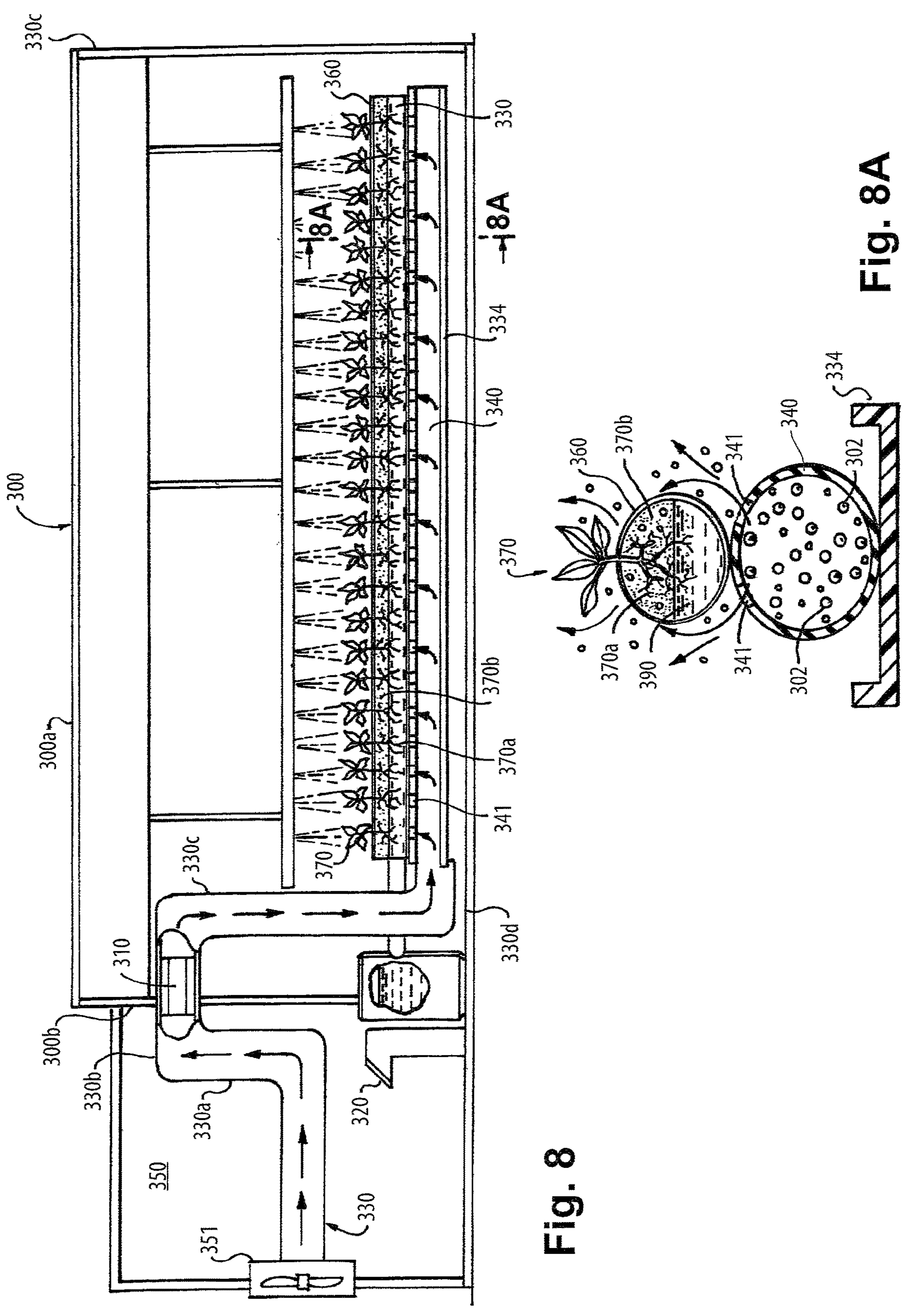
FIG. 8 is a diagrammatic side view and cross section of a greenhouse embodiment, using hydroxyl generators to provide hydroxyl radicals for growing plants.
FIG. 8A is an end view and crossection taken along view lines 8A-8A shown in FIG. 8 of the greenhouse embodiment of FIG. 8.

In another embodiment, as shown in FIGS. 8 and 8A, the hydroxyl generators can be used in greenhouses, for producing plants hydroponically, such as medicinal or other botanical plants, which are grown agriculturally inside a greenhouse. The plants are mounted in the greenhouse on troughs and tables, typically hydroponically, where the roots are held in place by media, such as coconut fibers, vermiculite, or other materials, so that a portion of the roots are soaked in hydroponic fluid, for irrigation and fertigation, and the upper part of the roots are exposed to air, which is brought through with hydroxyl radicals from the hydroxyl generators. For example, in FIG. 8, hydroxyl generator 310 (polygonal-shaped) is positioned in the greenhouse 300 in an air duct 330.

The greenhouse has a top roof area 300*a*, side walls 300*b* and 300*c*, and a base ground level 300*d*. The greenhouse 300 is adjacent to a utility room 350, which has utility controls 320 for controlling the electronics and mechanics of the system, as well as a hydroponic fluid source 390, which provides the hydroponic fluid through a pipe conduit 360. The pipe 360 has the lower parts of the roots and the media soaking in the fluid, with an upper portion of the roots and media being exposed to air of the plants 370, which have roots 370*a* held in place by media 370B. The hydroponic fluid 370*e* is provided through the hydroponic fluid pipe 360. The polygonal-shaped hydroxyl generators 310 are produced in an enclosed air duct, which is preferably a fan 351, and produces an airflow into an air duct 330, which emanates horizontally from the fan 351, or other air source, then makes an upward 90-degree turn, through an air duct portion 330*a*, which then turns at 90 degrees horizontally at an upper portion of the utility room 350 through a horizontal portion 330*b*, within which is located the hydroxyl generator, just before a further downward air duct portion 330*c* emanates downward to the level of trough 334 inside the greenhouse, so that the air from the downward portion 330*c* of the air duct is then sent horizontally through a flexible sock sleeve 340, having multiple upper apertures 341 to permit the radical hydroxyl flows below and then around the hydroponic fluid pipe, and then contacting the air and plant roots 370*a* of the plants 370, within the media, such as the coconut fiber 370*b*. Optionally, an overhead mister hose 365 may be provided in case the plants are not hydroponically bred. In any case, the hydroxyls, whether they are blown or pumped through the root system and media in the greenhouse trough in the hydroponic growing system in the greenhouse, the hydroxyl radicals are exposed to the portions of the roots 370*a* and growing media 370*b*, so that they can be misted exposed therein while being irrigated and/or fertigated, either hydroponically, or alternatively within conventional soil media. In this version, the greenhouse 300 is connected to the utility room 350. The hydroxyl generators are installed in a strategic position at the top of the air duct 330*b*, before the hydroxylated air is sent downward through portion 330*c* of undulating air duct 330 spanning from utility laboratory room 350 and greenhouse 300 and then the air filled with hydroxyls is sent to the flexible sock sleeve 340, having upper apertures 341 for release of the hydroxyls to intermingle with the plant roots 370*a* of the hydroponically grown plants 370 located above the parallel troughs 334 of greenhouse 300.

FIG. 8A shows a detailed view of the hydroxyl flexible sleeve 340, with hydroxyls 302 therein and the arrows indicate the flow of the hydroxyls around the lower portion of the pipe with the fertigation and irrigation fluids for the hydroponics where the lower levels of the roots 370*a* are provided, but where the upper level of the roots exposed to air within the media 370*b* are then exposed to the hydroxyls of the plants 370. The trough 334 is shown below the flexible sock sleeve 340. The hydroxyls are introduced into air surrounding exposed roots, leaves, stems, vascular or phloem tissues of the plant.

Figure 9:
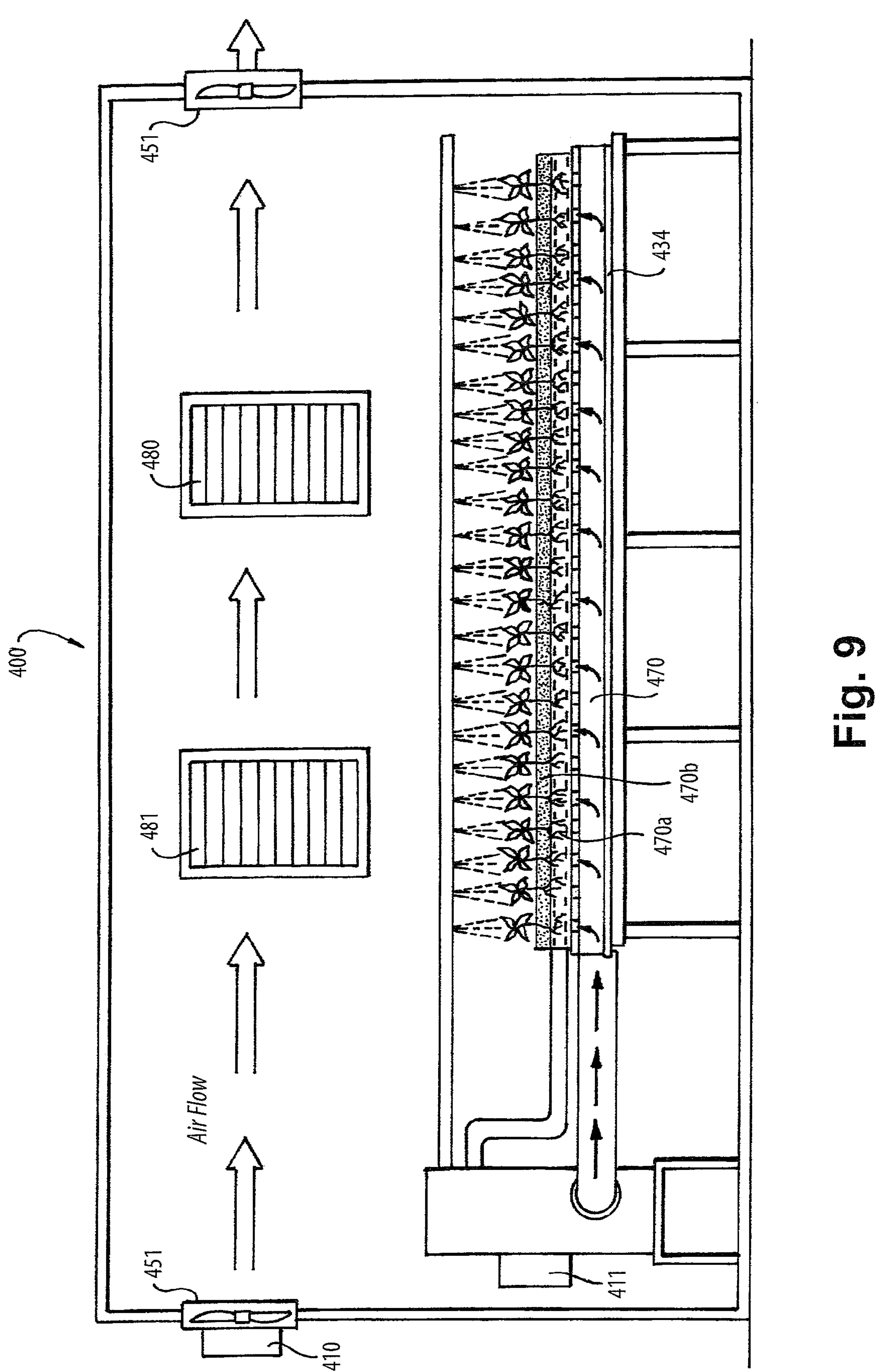
FIG. 9 is a perspective view of an alternate embodiment for a greenhouse for using hydroxyl generators for treating plants.

In an alternate embodiment in a non-hydroponic system, as shown in FIG. 9, a greenhouse 400 includes hydroxyl generators 410 and 411, which are provided either adjacent to an intake fan 451 for airflow through and out the greenhouse 400 through exhaust fan 451 and/or motorized or pressurized shutter outlets 480, 481. A trough 434 is provided for the plants and there may be a drip irrigation hose 470 with apertures for irrigation of hydroponic growing media 470*c* of the roots 470*a* of plants 470, where the hydroxyls less generated by hydroxyl generator 411 will mingle within the air exposed portions of the roots and in the media 470*b* of the plants 470. Optional hydroxyl generator 410 can be located at the intake fan for sending the hydroxyls through the airflow of the greenhouse 400 in areas above the plants.

The hydroxyl generators shown in FIGS. 1-9 will inactivate any VOCs or pathogens, such as virus, bacteria or fungi, anywhere in the air of the buildings FIG. 103, or having the controls of FIG. 4, as well as in small units where the portable housings are provided for the hydroxyl generators.

In addition, in the greenhouse embodiment, the hydroxyl generators are provided so that the hydroxyl radicals will flow adjacent to and through the media of the plants being farmed therein.

In the foregoing description, certain terms and visual depictions are used to illustrate the preferred embodiment. However, no unnecessary limitations are to be construed by the terms used or illustrations depicted, beyond what is shown in the prior art, since the terms and illustrations are exemplary only, and are not meant to limit the scope of the present invention.

It is further known that other modifications may be made to the present invention, without departing the scope of the invention, as noted in the appended Claims

We claim:

1. A method for decontaminating/neutralizing breathable air comprising the steps of:

creating an access opening in an air duct in a building;

forming a hydroxyl radical generator;

forming a generator mounting bracket;

inserting the generator mounting bracket through the access opening and securing the generator mounting bracket to a wall of the air duct;

inserting the hydroxyl radical generator through the access opening and mounting the hydroxyl radical generator with respect to the wall of the air duct using the generator mounting bracket for thereby receiving a flow of air from a first portion of the air duct into an air inlet of the hydroxyl radical generator and for delivering decontaminated air out from an air outlet of the hydroxyl radical generator into a second portion of the duct;

forming the hydroxyl radical generator with a housing having a linearly elongated shape with the air inlet at one end of the elongated housing and the air outlet at an opposite end of the elongated housing;

forming the linearly elongated shape of the housing of the hydroxyl generator with a polygonal cross-sectional shape having a constant cross-sectional opening at and between each of the air inlet and the air outlet permitting air flow being unrestricted by the housing;

forming the polygonal cross-sectional shape of the housing with eight sides, and forming the eight sides of the housing into an octagonal cross-sectional shape with reflective interior surfaces;

providing said hydroxyl radical generator with a plurality of UV lamps, being a first UV lamp, a second UV lamp, a third UV lamp, and a fourth UV lamp, and forming each UV lamp with a tubular bulb made of quartz;

emitting ultraviolet light from each of the plurality of UV lamps in the spectrum of between 100 and 400 nanometers for generating hydroxyl radicals from water vapor contained within the flow of air, resulting in deactivating of chemicals and pathogens in the air flow using the hydroxyl radicals;

forming a first mounting bracket and a second mounting bracket each with a first flange, and a second flange being oriented perpendicular to the first flange;

securing the first flange of the first mounting bracket to a side of the housing in proximity to a first end of said housing, with the first flange extending perpendicular to the side of the housing;

securing the first flange of the second mounting bracket to the side of the housing in proximity to a second end of the housing;

symmetrically positioning and securing a first UV lamp fastener and a second UV lamp fastener onto a top surface of the second flange of the first mounting bracket;

symmetrically positioning and securing a third UV lamp fastener and a fourth UV lamp fastener to a bottom surface of the second flange of the second mounting bracket;

symmetrically positioning and securing a fifth UV lamp fastener and a sixth UV lamp fastener to a top surface of the second flange of the second mounting bracket;

securing a seventh UV lamp fastener and an eighth UV lamp fastener to a bottom surface of second flange of the second mounting bracket;

mounting a first end of each of the first and second UV lamps to a respective one of the first and second UV lamp fasteners, and mounting a second end of each of the first and second UV lamps to a respective one of the fifth and sixth lamp fasteners;

mounting a first end of each of the third and fourth UV lamps to a respective one of the third and fourth UV lamp fasteners, and mounting a second end of each of the third and fourth UV lamps to a respective one of the seventh and eighth lamp fasteners;

mounting each of the first and second brackets and each of the UV lamp fasteners for thereby positioning each of the UV lamps with an axial direction of each UV lamp extending parallel to a lengthwise direction of said housing and thereby being parallel to the direction of the air flow in the air duct, and with each of the UV lamps being at a distance away from each of the eight sides of the octagonal cross-sectional shape of the housing, and being separated from each other;

forming the generator mounting bracket with a first flange, and a second flange and a third flange each extending perpendicularly away from respective distal ends of the first flange for thereby forming a channel-shaped cross-section, and with a fourth flange extending away from a distal end of the second flange, a fifth flange extending away from a distal end of the third flange, and a sixth flange extending away from the end of the fifth flange; and forming the third flange and the fourth flange at angles matching first and second sides of the octagonal-shaped housing, and forming the sixth flange at an angle matching and supporting a bottom of the octagonal-shaped housing;

mounting the first flange of the generator mounting flange to a side wall of the air duct, thereby centrally positioning the hydroxyl generator with respect to the first side wall and a second side wall of the duct, permitting air flow between the first side wall of the air duct and the housing of the hydroxyl generator, and permitting air flow between the second side wall of the air duct and the housing of the hydroxyl generator;

forming the lengthwise direction of the housing longer than its width; and forming each of said plurality of UV lamps with a length extending substantially from the first end of the housing to the second end of the housing, for decontaminating the air in the airflow across substantially the entire lengthwise direction of the housing.

2. The method as in claim 1, further comprising the step of:

using a detector for monitoring if a flow of air is detected within the housing, and shutting off the plurality of UV lamps when there is no flow of air in the housing.

3. The method as in claim 2, further comprising the steps of:

coupling an electronic controller with each of said plurality of UV lamps;

configuring the electronic controller for communicating wirelessly with each of the plurality of UV lamps; and electronically controlling the operation of each of the plurality of UV lamps using the electronic controller.

4. The method according to claim 2, further comprising the steps of:

mounting a sensor in said housing for sensing occurrence of an intrusion of VOCs into the housing;

using the controller for causing operation of only the first and second UV lamps when a flow of air is detected by the detector; and using the controller for causing operation of each of the first, second, third, and fourth UV lamps when the intrusion of VOCs into the housing is sensed by the sensor.

* * * * *